United States Patent
Hecht et al.

(10) Patent No.: US 10,647,650 B2
(45) Date of Patent: *May 12, 2020

(54) PROCESS FOR HYDROFORMYLATING SHORT-CHAIN OLEFINS USING A HETEROGENIZED CATALYST SYSTEM WITHOUT IONIC LIQUID

(71) Applicant: Evonik Operations GmbH, Essen (DE)

(72) Inventors: Corinna Hecht, Haltern am See (DE); Robert Franke, Marl (DE); Frank Stenger, Alzenau (DE); Peter Kreis, Dortmund (DE); Jennifer Haßelberg, Dortmund (DE); Marc Oliver Kristen, Haltern am See (DE)

(73) Assignee: Evonik Operations GmbH, Essen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 16/577,082

(22) Filed: Sep. 20, 2019

(65) Prior Publication Data

US 2020/0109102 A1 Apr. 9, 2020

(30) Foreign Application Priority Data

Oct. 5, 2018 (EP) .................................. 18198787

(51) Int. Cl.
| | |
|---|---|
| *C07C 45/50* | (2006.01) |
| *B01J 21/00* | (2006.01) |
| *B01J 27/00* | (2006.01) |
| *B01J 31/18* | (2006.01) |
| *B01J 27/224* | (2006.01) |
| *B01J 31/02* | (2006.01) |
| *B01J 35/04* | (2006.01) |
| *B01J 21/08* | (2006.01) |

(52) U.S. Cl.
CPC ............. *C07C 45/505* (2013.01); *B01J 21/08* (2013.01); *B01J 27/224* (2013.01); *B01J 31/0237* (2013.01); *B01J 31/185* (2013.01); *B01J 35/04* (2013.01); *B01J 2231/321* (2013.01); *B01J 2531/822* (2013.01)

(58) Field of Classification Search
CPC ........ C07C 45/50; C07C 45/505; B01J 21/08; B01J 27/224
See application file for complete search history.

(56) References Cited

U.S. PATENT DOCUMENTS

| | | | |
|---|---|---|---|
| 4,012,450 | A | 3/1977 | Bond et al. |
| 9,676,805 | B2 | 6/2017 | Dyballa et al. |
| 9,845,276 | B2 | 12/2017 | Franke et al. |
| 10,155,200 | B2 | 12/2018 | Geilen et al. |
| 10,245,578 | B2 | 4/2019 | Klasovsky et al. |
| 2016/0257634 | A1 | 9/2016 | Dyballa et al. |
| 2016/0257637 | A1 | 9/2016 | Mosler et al. |
| 2019/0169104 | A1 | 6/2019 | Fridag et al. |
| 2019/0169105 | A1 | 6/2019 | Fridag et al. |
| 2019/0169106 | A1 | 6/2019 | Fridag et al. |

FOREIGN PATENT DOCUMENTS

| | | |
|---|---|---|
| DE | 2055539 A1 | 5/1977 |
| WO | 2015/028284 A1 | 3/2015 |

OTHER PUBLICATIONS

European Search Report dated Feb. 12, 2020 in EP 19200444.8 (7 pages).
Sandee et al., "ROTACAT: A Rotating Device Containing a Designed Catalyst for Highly Selective Hydroformylation," copyright 2001, Adv. Synth. Catal., vol. 343, No. 2, pp. 201-206 (6 pages).
Nadolny et al., U.S. Appl. No. 16/291,144, filed Mar. 4, 2019.
Nadolny et al., U.S. Appl. No. 16/293,702, filed Mar. 6, 2019.
Nadolny et al., U.S. Appl. No. 16/293,859, filed Mar. 6, 2019.
Nadolny et al., U.S. Appl. No. 16/509,532, filed Jul. 12, 2019.
Hasselberg et al., U.S. Appl. No. 16/574,217, filed Sep. 18, 2019.

*Primary Examiner* — Sikarl A Witherspoon
(74) *Attorney, Agent, or Firm* — Nexsen Pruet PLLC; Philip P. McCann

(57) ABSTRACT

The invention relates to a process for hydroformylating short-chain olefins, especially C2 to C5 olefins, in which the catalyst system is in heterogenized form on a support of a porous ceramic material, and to plants for performing this process.

20 Claims, No Drawings

US 10,647,650 B2

PROCESS FOR HYDROFORMYLATING SHORT-CHAIN OLEFINS USING A HETEROGENIZED CATALYST SYSTEM WITHOUT IONIC LIQUID

CROSS REFERENCE TO RELATED APPLICATIONS

This application is a 35 U.S.C. § 119 patent application which claims the benefit of European Application No. 18198787.6 filed Oct. 5, 2018, which is incorporated herein by reference in its entirety.

FIELD

The project that led to this patent application was financed under Grant Agreement No. 680395 from the European Union Horizon 2020 Research and Innovation Programme.

The present invention relates to a process for hydroformylating short-chain olefins, especially C2 to C5 olefins, in which the catalyst system is present in heterogenized form on a support of a porous ceramic material, and to plants for performing this process.

BACKGROUND

Hydroformylation is one of the most important reactions in industrial scale chemistry, having an annual global production capacity of several million tonnes. This involves reacting alkenes (olefins) with a mixture of carbon monoxide and hydrogen (also: synthesis gas or syngas) using a catalyst to give aldehydes, which are important and valuable intermediates in the production of chemical bulk products such as alcohols, esters or plasticizers.

Hydroformylation is conducted exclusively under homogeneous catalysis on the industrial scale. The soluble transition metal catalyst systems are typically based on cobalt or rhodium, which is often used together with phosphorus-containing ligands, for example phosphines or phosphites, for the hydroformylation of comparatively short-chain olefins.

There are various problems in the known processes, and these are especially linked to the fact that both rhodium and cobalt and compounds thereof are comparatively costly. There is a high level of energy expenditure and complex chemical engineering in order to very substantially avoid losses of catalyst during the hydroformylation process, for example by catalyst recycling steps, some of them very complex. Moreover, product purification steps are becoming more complex in order to ensure that as far as possible no catalyst residues remain in the product.

Further problems with the known homogeneously catalysed processes are the stability of the ligands, which have to withstand the hydroformylation conditions, such as temperature, pressure, pH etc., and consumption of the solvent used during the process, which can be compensated for by replenishment.

In order to get round the aforementioned problems in the homogeneously catalysed hydroformylation, there has been development of hydroformylation methods in which the catalyst is heterogenized, especially by immobilization on a support material (cf. introductory discussion in WO 2015/028284 A1). The terms "heterogenization" and "immobilization" should accordingly be understood such that the catalyst is immobilized by formation of a thin liquid film with the aid of an ionic liquid on the surface and/or in the pores of a solid support material and there is no reaction solution in the conventional sense in which the catalyst is homogeneously dissolved.

With regard to the immobilization/heterogenization, the already mentioned WO 2015/028284 A1 discloses what are called SILP systems (SILP=Supported Ionic Liquid Phase), in which the catalyst system is immobilized with rhodium, iridium or cobalt as central atom, especially on a porous silicon dioxide support using an ionic liquid.

It is thought that the ionic liquid acts as a catalyst carrier/as a solvent, thus helping to immobilize the catalyst system on the support. However the problem with ionic liquids is that these are comparatively expensive and in some cases not toxicologically harmless.

The problem addressed by the present invention was that of providing a single-stage or multistage hydroformylation process in which a heterogenized catalyst system that does not have the aforementioned problems is used in a hydroformylation step.

SUMMARY

This problem is solved according to the present invention in that a single-stage or multistage hydroformylation process comprises at least one hydroformylation step in which a catalyst system in heterogenized form on a support of a porous ceramic material is used without ionic liquid.

DETAILED DESCRIPTION

The present invention thus provides a process for hydroformylating C2 to C5 olefins, wherein the hydroformylation comprises one or more hydroformylation steps, characterized in that in at least one hydroformylation step a feed mixture comprising the C2 to C5 olefins is subjected to a hydroformylation with synthesis gas in the presence of a catalyst system comprising a metal from group 8 or 9 of the Periodic Table of the Elements, at least one organic phosphorus-containing ligand and a stabilizer, in a reaction zone, wherein the feed mixture and the synthesis gas are passed over a support composed of a porous ceramic material on which the catalyst system is in heterogenized form, the catalyst system comprises no ionic liquid; and the support is a monolith, i.e. a block of a ceramic material, to which a washcoat composed of the same or a different ceramic material with respect to the ceramic material of the support is applied.

The feed mixture used may be any mixture comprising C2 to C5 olefins, especially ethene, propene, 1-butene, 2-butene, 1-pentene or 2-pentene, as reactants. The amount of olefins in the feed mixtures should naturally be high enough to be able to economically conduct a hydroformylation. This especially includes technical mixtures from the petrochemical industry, for example raffinate streams (raffinate I, II or III) or crude butane. According to the present invention, crude butane comprises 5% to 40% by weight of butenes, preferably 20% to 40% by weight of butenes (the butenes are composed of 1% to 20% by weight of 1-butene and 80% to 99% by weight of 2-butene), and 60% to 95% by weight of butanes, preferably 60% to 80% by weight of butanes.

In the case of an at least two-stage hydroformylation feed mixtures may also be (gaseous) outputs from another hydroformylation. If the process according to the invention comprises at least two hydroformylation steps the step in which the catalyst system heterogenized on a support made of a porous ceramic material is used without ionic liquid is at least the second hydroformylation step. The olefins unconverted in the first hydroformylation step may then still be converted using the catalyst system according to the invention. Between the hydroformylation steps there may be arranged a physical separation with which the gaseous output from the first hydroformylation is separated into at least one phase rich in unconverted olefins and at least one phase rich in product aldehyde. The phase rich in unconverted olefins is then subjected to the second hydroformylation.

The catalyst system used in the hydroformylation step according to the invention preferably comprises a transition metal from group 8 or 9 of the Periodic Table of the Elements, especially iron, ruthenium, iridium, cobalt or rhodium, more preferably cobalt or rhodium, at least one organic phosphorus-containing ligand and a stabilizer.

The stabilizer is preferably an organic amine compound, more preferably an organic amine compound containing at least one 2,2,6,6-tetramethylpiperidine unit of formula (I):

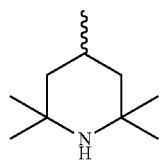
(I)

In a particularly preferred embodiment of the present invention, the stabilizer is selected from the group consisting of the compounds of the following formulae (I.1), (I.2), (I.3), (I.4), (I.5), (I.6), (I.7) and (I.8):

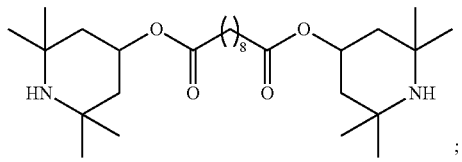
(I.1)

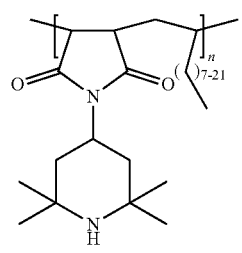
(I.2)

where n is an integer from 1 to 20;

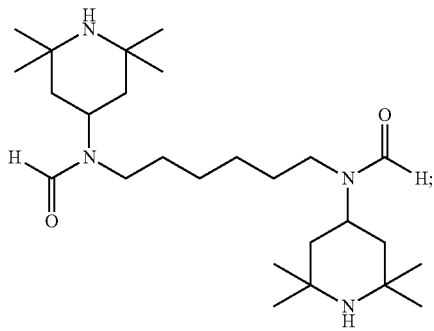
(I.3)

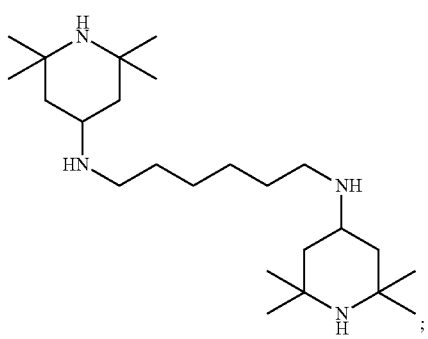
(I.4)

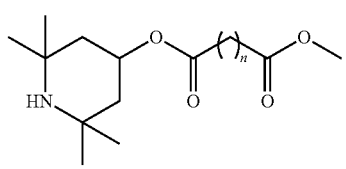
(I.5)

where n is an integer from 1 to 12;

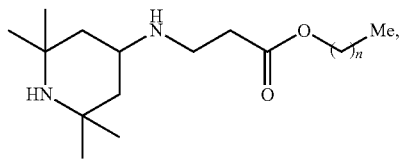
(I.6)

where n is an integer from 1 to 17;

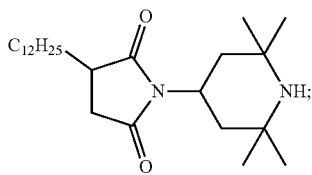
(I.7)

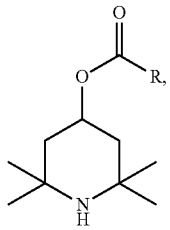

where R is a C6- to C20-alkyl group.

For all film-forming components, i.e. in this case the stabilizer, the gas solubility for the reactants should be better than the gas solubility of the products. In that way alone, it is possible to achieve partial physical separation between reactant olefins used and product aldehydes formed. In principle, other film-forming substances would also be conceivable for the purpose, but it should be ensured that there is no elevated high boiler formation and/or that the resupply of the reactant olefins is restricted.

The organic phosphorus-containing ligand for the catalyst system preferably has the general formula (VI)

where R', R" and R'" are each organic radicals, with the proviso that R' and R'" are not identical, and each A is a bridging —O—P(—O)$_2$— group, where two of the three oxygen atoms —O— are respectively bonded to R' radical and R'" radical. The organic R', R", R'" radicals preferably do not contain a terminal trialkoxysilane group.

In a preferred embodiment, R', R" and R'" in the compound of the formula (VI) are preferably selected from substituted or unsubstituted 1,1'-biphenyl, 1,1'-binaphthyl and ortho-phenyl groups, especially from substituted or unsubstituted 1,1'-biphenyl groups, with the proviso that R' and R'" are not identical. More preferably, the substituted 1,1'-biphenyl groups in the 3,3' and/or 5,5' positions of the 1,1'-biphenyl base skeleton have an alkyl group and/or an alkoxy group, especially a C1-C4-alkyl group, more preferably a tert-butyl and/or methyl group, and preferably a C1-C5-alkoxy group, more preferably a methoxy group.

According to the invention, the aforementioned catalyst system is in heterogenized form on a support of a porous ceramic material. In the context of the present invention, the expression "heterogenized on a support" is understood to mean that the catalyst system is immobilized via formation of a thin, solid or liquid film with the aid of a stabilizer on the inner and/or outer surface of a solid support material. The film may also be solid at room temperature and liquid under reaction conditions.

The inner surface of the solid support material especially comprises the inner surface area of the pores and/or channels. The concept of immobilization includes both the case that the catalyst system and/or the catalytically active species is in dissolved form in the solid or liquid film and the case that the stabilizer acts as an adhesion promoter or the catalyst system is adsorbed on the surface, but is not in chemically or covalently bound form on the surface.

According to the invention, there is thus no reaction solution in the conventional sense in which the catalyst is homogeneously dissolved; instead, the catalyst system is dispersed on the surface and/or in the pores of the support.

The porous ceramic material is preferably selected from the group consisting of a silicate ceramic, an oxidic ceramic, a nitridic ceramic, a carbidic ceramic, a silicidic ceramic and mixtures thereof.

The silicate ceramic is preferably selected from aluminosilicate, magnesium silicate, and mixtures thereof, for example bentonite. The oxidic ceramic is preferably selected from γ-alumina, α-alumina, titanium dioxide, beryllium oxide, zirconium oxide, aluminium titanate, barium titanate, zinc oxide, iron oxides (ferrites) and mixtures thereof. The nitridic ceramic is preferably selected from silicon nitride, boron nitride, aluminium nitride and mixtures thereof. The carbidic ceramic is preferably selected from silicon carbide, boron carbide, tungsten carbide or mixtures thereof. Also conceivable are mixtures of carbidic and nitridic ceramic, called the carbonitrides. The silicidic ceramic is preferably molybdenum silicide. The support according to the present invention to which the catalyst system is applied preferably consists of a carbidic ceramic.

The support is a monolith, meaning that the support of the porous ceramic material consists of a block (a three-dimensional object) of a ceramic material. The block may either be in one-piece form or consist of multiple, i.e. at least two, individual parts that may be joined together to form the block and/or may be joined to one another in a fixed or partable manner. But the support is more particularly not a granular material that can be used as catalyst bed in fixed bed reactors.

The support of the porous ceramic material is preferably a component that extends in three dimensions and may in principle have any geometric shapes in its cross section, for example round, angular, square or the like. The component that extends in three dimensions and can be used as support, in a preferred embodiment, has a longitudinal direction (direction of the longest extent) in main through-flow direction (direction in which the feed mixture and the synthesis gas flow from the reactor inlet to the outlet).

The support thus formed from the porous ceramic material has at least one continuous channel in main through-flow direction. However, the channel(s) may also be configured such that they are not completely continuous but are concluded at the opposite end from the reactor inlet, or the channel is closed toward this end. The support may also have at least two or more channels. The diameter of the channels may be in the range from 0.25 to 50 mm, preferably in the range from 1 to 30 mm, further preferably in the range from 1.5 to 20 mm and more preferably in the range from 2 to 16 mm. If a plurality of channels are present, the diameters of the channels may be the same or different. The diameter of the channels should especially be chosen by comparison with the diameter(s) of the overall support in such a way that mechanical stability is not impaired.

Furthermore, the support of the ceramic material is porous, i.e. has pores. The catalyst system according to the invention is especially also in the liquid or solid film in these pores. The pore diameter is preferably in the range from 0.9 nm to 30 μm, preferably in the range from 10 nm to 25 μm and more preferably in the range from 70 nm to 20 μm. Pore diameter can be determined by means of nitrogen adsorption or mercury porosimetry to DIN 66133 (1993-06 version).

In a preferred embodiment, the support has at least partly continuous pores that extend from the surface to the channels and/or from one channel to the next channel(s). It is also possible that multiple pores are connected to one another and hence overall form a single continuous pore.

The production of the support from a porous ceramic material on which the catalyst system is in heterogenized form is effected as described below: What is called a washcoat is additionally applied to the support composed of the ceramic material, and is composed of the same or a different ceramic material with respect to the ceramic material of the support, especially a ceramic material selected from the aforementioned ceramic materials, preferably silicon oxide. The washcoat itself may be porous or nonporous; preferably the washcoat is nonporous. The particle size of the washcoat is preferably 5 nm to 3 µm, preferably 7 nm to 700 nm. The washcoat is used to introduce or to generate the desired pore size and/or to increase the surface area of the support. The washcoat can especially be applied by means of dipping (dip-coating) into a washcoat solution containing the ceramic material of the washcoat, possibly also as a precursor. The amount of the washcoat on the support is ≤20% by weight, preferably ≤15% by weight, more preferably ≤10% by weight, based on the overall amount of the support.

The catalyst system is applied to the ceramic support thus produced with the washcoat applied. For this purpose, a catalyst solution is first produced by mixing, especially at room temperature and ambient pressure, comprising at least one organic phosphorus-containing ligand, at least one metal precursor, for example chlorides, oxides, carboxylates of the respective metal, at least one stabilizer and at least one solvent. According to the invention, the catalyst solution is explicitly made up without ionic liquid. The catalyst solution should especially be prepared in an inert environment, for example a glovebox. "Inert environment" in this case means a very substantially water- and oxygen-free atmosphere.

The solvent may be chosen from all solvent classes (protic, aprotic, polar or nonpolar). A prerequisite for the solvent is the solubility of catalyst system (ligand, metal precursor and stabilizer) and preferably also of the high boilers formed in the hydroformylation. Solubility can be increased within the immobilization step by heating.

The solvent is preferably aprotic and polar, for example acetonitrile and ethyl acetate, or else aprotic and nonpolar, for example THF and diethyl ether. It is also possible to use hydrochlorocarbons, for example dichloromethane, as solvent.

The catalyst solution thus prepared is then contacted with the support (optionally including washcoat), for example by dipping (dip-coating) or by means of filling in a pressure vessel, for example directly in the reactor (in situ impregnation). If the catalyst solution is applied outside the reactor, the support must of course be installed into the reactor after the solvent has been removed. Preferably, the catalyst solution is applied directly to the support with the washcoat in the reactor because this can avoid possibly time-consuming installation and deinstallation steps and possible contamination of the catalyst.

In the case of in situ impregnation, the reactor, prior to the filling, is purged with an inert gas, for example noble gases, alkanes or nitrogen. The purging can be conducted at 1 to 25 bar, preferably under a slightly positive pressure of 20 to 90 mbar, more preferably 30 to 60 mbar, above standard pressure. The reactor can be cooled down prior to the purging with inert gas in order to prevent the solvent in the catalyst solution to be introduced from evaporating immediately. However, if the solvent has a boiling temperature greater than the reactor temperature, the cooling of the reactor can be dispensed with.

After the purging with inert gas, the pressure present can be released, for example via the pressure control system, preferably until the reactor is unpressurized, i.e. at ambient pressure (i.e. 1 bar). Otherwise, it is also possible to generate a vacuum in the reactor, for example with a vacuum pump. In one configuration of the present invention, the reactor can again be purged with an inert gas as described above after the pressure has been released or after evacuation. This operation of releasing pressure/evacuating and purging again can be repeated as often as desired.

For the filling of the reactor, the catalyst solution is initially charged in a pressure vessel and preferably pressurized to a positive inert gas pressure of 1 to 25 bar, more preferably a slightly positive inert gas pressure of 20 to 90 mbar, preferably 30 to 60 mbar, above reactor pressure. The inert gas may be a noble gas, an alkane, for example butane, or nitrogen. The catalyst solution is then introduced into the reactor at said positive pressure to which the pressure vessel has been pressurized, especially in a pressure-driven manner. The pressure in the pressure vessel on filling should be higher than in the reactor. Temperatures may be in the range from 20 to 150° C., and pressure from 1 to 25 bar.

Another means of filling is that the reactor is kept under reduced pressure after purging with inert gas and the catalyst solution is drawn into the reactor by virtue of the reduced pressure. For the preparation of the catalyst solution, a solvent that boils under the prevailing vacuum or reduced pressure and the prevailing temperatures should be used.

The reactor can be filled with the catalyst solution via the normal inlets/outlets. Liquid distributors or nozzles within the reactor can ensure homogeneous distribution of the catalyst liquid, as can pressure drop internals or regulators for the metering rate that are optionally present. After the catalyst system has been applied, the solvent is removed. This involves firstly discharging the remaining catalyst solution via the reactor outlet. Thereafter, solvent residues remaining in the reactor are evaporated by adjusting the pressure or increasing the temperature. In another embodiment, the adjustment of the pressure can also be conducted with a simultaneous increase in temperature. Depending on the solvent, the temperature may be 20 to 150° C. Depending on the solvent, the pressure may be adjusted to a high vacuum ($10^{-3}$ to $10^{-7}$ mbar), but according to the solvent and temperature, elevated pressures of a few mbar up to several mbar are also conceivable.

The stabilizer remains in heterogenized form on the support with the catalyst composed of the metal, especially cobalt or rhodium, and the organic phosphorus-containing ligand.

The catalyst system can be applied to the support either directly in the reactor (in situ) or outside the reactor. In a preferred embodiment of the present invention, the catalyst system is applied directly in the reactor, i.e. in situ. After the solvent has been removed, the reactor can be used immediately and charged with the feed mixture. This has the advantage that no time-consuming installation and deinstallation steps that would result in a prolonged reactor shutdown are needed. Moreover, the size of the support in that case is no longer limited in that suitable spaces with inert environments are available in a particular size. The size of the support can be chosen freely depending on the reactor design. A further problem is that the support must always be transported with exclusion of air, which is sometimes difficult to achieve.

On completion of application of the catalyst system to the support and of removal of the solvent, the plant, especially the reactor, can be run up, i.e. put into operation, by a two-stage or multistage startup procedure.

The aim of the startup procedure is gentle activation of the catalyst system and attenuation of the maximum starting activity of the catalyst to prolong the service life of the catalyst system. Moreover, the startup procedure is intended to prevent the formation of a liquid phase since this can lead to deactivation, blocking and/or washout of the catalyst system. This is because, particularly in the case of startup of a freshly produced catalyst system (on the support) with concentrated reactant, it is possible to attain a reaction conversion maximum which is also associated with maximum formation of by-products (high boilers). If the proportion of the high-boiling by-products, depending on the operating conditions (pressure and temperature), exceeds a certain value, the result of this, owing to the vapour pressures of the individual components that are dependent on the mixture present, can be the formation of a liquid phase that can damage, block or wash out the catalyst system.

According to the invention, the activation of the catalyst system is preferably implemented with a rising conversion over a prolonged period of time. Thus, for any combination of pressure, temperature and composition of the feed mixture, it is possible to calculate a maximum permissible conversion for the formation of by-products that must not be exceeded in order not to allow the aforementioned problems to arise. The conversion for the formation of by-products can also be ascertained depending on the conversion for the formation of the product aldehydes (=depending on the aldehyde concentration), meaning that the startup procedure is guided by the maximum conversion of the feed olefins.

In the case of known long-term operating conditions of the reactor that enable a reliable degree of conversion of the feed olefins of 20% to 95%, preferably of 80%-95%, the startup procedure can be implemented in such a way that the composition of the feed mixture which is run into the reactor is altered stepwise without exceeding the maximum conversion of the feed olefins.

It is possible here to vary the composition of the feed mixture that ensures a reliable conversion of the olefins under long-term operating conditions in such a way that, at a constant volume flow rate, the olefin content and/or the synthesis gas content is raised in at least two stages, preferably more than three, especially four or more stages, without exceeding the maximum conversion of the feed olefins. For this purpose, the technical feed mixture and synthesis gas mixture may be supplied in the first stage(s) with inert gases, for example $N_2$, argon, helium or the like.

Catalyst activity can decrease with increasing operating time, for example as a result of the enrichment of high boilers and/or the coverage or deactivation of active sites. The high boilers can lead to increased condensation in the pores, such that the pores are accessible to the reactant olefins more slowly, if at all. Secondly, some by-products can lead to breakdown of the catalyst system, which likewise decreases the activity of the catalyst. A decrease in catalyst activity can be ascertained, for example, from the drop in conversions or selectivities, especially via an appropriate analysis by means of Raman spectroscopy, gas chromatography or mass flow meters (MFMs). Another option would be model-based monitoring of the catalyst activity. This would be a method independent of the operating conditions for monitoring the catalyst activity, but also in order to extrapolate the progression and hence support review/regeneration planning.

In the case of inadequate catalyst activity, the catalyst system in heterogenized form on the porous ceramic support can be exchanged. For this purpose, the catalyst or support can be purged once or more than once with a solvent in the reactor. The purging can demobilize and remove the catalyst system. The solvent may be one of the solvents mentioned for the preparation of the catalyst solution. The temperature on solvent purging may be 20 to 150° C. The pressure on solvent purging may additionally be 1 to 25 bar.

After the purge, the support is reimpregnated once or more than once, especially by the above-described in situ impregnation of the support. The in situ impregnation is thus renewed and the heterogenized catalyst system is freshly applied. The in situ reimpregnation can be conducted under exactly the same conditions as described above for the first in situ impregnation.

Owing to the fact that the catalyst system is fully exchanged by purging and reapplication, these steps can constantly be repeated as soon as the catalyst activity drops again. A further advantage is that both high boilers and product aldehydes and breakdown products of the catalyst system can be discharged. However, it should be ensured that the properties of the support are not impaired by demobilization and in situ reimpregnation. Otherwise, exchange of the porous ceramic support would have to be conducted.

A further option is that the overall porous ceramic support on which the catalyst system is in heterogenized form is exchanged. The catalyst system in heterogenized form on the support (removed from the reactor) can then be exchanged as described above outside the reactor and stored until the next installation and use in the reactor. As mentioned above, an inert environment is required on application of the catalyst system, and therefore the handling and storage in the procedure mentioned of deinstallation and installation of the support should be effected under corresponding conditions.

In principle, it is preferred to conduct a process in which there are multiple reactors in parallel in the reaction zone and these are used alternately. This involves using at least one reactor (a) for the hydroformylation according to the invention, i.e. one which is in operation, and at least one reactor (b) which is in the wait state. This is understood to mean that, as soon as catalyst activity is found to no longer be sufficient in reactor (a) which is in operation, the stream of the feed mixture is switched from this reactor (a) to the next reactor (b) in the wait state that is put into operation therewith. Reactor (a) is then transferred to regeneration mode, where the catalyst system is regenerated or demobilized as described and the support is newly impregnated, and then transferred into the wait position until it is swapped again with reactor (b). This principle can also be applied to 3 or more reactors, where at least one reactor is in operation, one or more reactors are simultaneously in the wait state and one or more reactors are simultaneously in regeneration mode.

The second hydroformylation step is preferably conducted under the following conditions: The temperature in the second hydroformylation step should be in the range from 65 to 200° C., preferably 75 to 175° C. and more preferably 85 to 150° C. The pressure should not exceed 35 bar, preferably 30 bar, more preferably 25 bar, during the second hydroformylation step. The molar ratio between synthesis gas and the second feed mixture should be between 6:1 and 1:1. Optionally, the feed mixture can be diluted with inert gas, for example the alkanes present in technical hydrocarbon streams.

A gaseous output comprising at least a portion of the product aldehydes formed and at least a portion of the unconverted olefins is preferably withdrawn continuously from the reaction zone in which the hydroformylation according to the invention is conducted. The gaseous output may be subjected to one or more physical separation step(s) in which the gaseous output is separated into at least one phase rich in unconverted olefins and at least one phase rich in product aldehyde.

The physical separation can be conducted by known physical separation methods such as condensation, distillation, centrifugation, nanofiltration or combinations of two or more of these, preferably condensation or distillation.

In the case of a multistage physical separation, the phase rich in product aldehyde which is formed in the first physical separation is sent to a second physical separation, especially a downstream removal of aldehyde, in which the product aldehyde is separated from the other substances present in this phase, frequently alkanes and reactant olefins. The phase rich in unconverted olefin can be recycled to the hydroformylation step or, in the case of a multistage configuration, to one of the hydroformylation steps in order to hydroformylate the olefins present therein to the product aldehyde as well.

In the physical separation, as well as the phases mentioned, it is also possible to withdraw a purge gas stream having a composition identical or at least similar to the phase rich in unconverted olefin. The purge gas stream can likewise be guided to the second physical separation or aldehyde removal in order to remove the product aldehyde present therein and in order to discharge impurities (e.g. nitrogen in the synthesis gas) or inert substances (e.g. alkanes in the feed mixture) from the system. The impurities or inert substances can typically be removed in the second physical separation as volatile substances, for example at the top of a column.

The present invention also further provides a plant with which the present process can be conducted and which especially comprises a reactor in which the hydroformylation step according to the invention is conducted. In addition, the plant may comprise a physical separation unit with which the gaseous output from the hydroformylation step is separated into at least one phase rich in unconverted olefin and at least one phase rich in product aldehyde, where this physical separation unit is arranged downstream of the hydroformylation step according to the invention. Downstream of the first physical separation, there may be a second physical separation unit, especially an aldehyde removal unit, with which the product aldehyde is removed.

Even without further elaboration it is assumed that a person skilled in the art will be able to utilize the description above to the greatest possible extent. The preferred embodiments and examples are therefore to be interpreted merely as a descriptive disclosure which is by no means limiting in any way whatsoever.

The present invention is more particularly elucidated hereinbelow with reference to examples. Alternative embodiments of the present invention are obtainable analogously.

EXAMPLE

Experiment 1: Preparation and Analysis of a Catalyst System not According to the Invention with Ionic Liquid The support used was a monolith of silicon carbide having a length of about 20 cm and a diameter of about 25 mm. The support was porous and was pretreated with a washcoat ($SiO_2$). The support had 31 channels having a diameter of about 3 mm. The support was inserted into a reactor and contacted with a catalyst solution containing Rh(acac)(CO)$_2$, Biphephos (ligand), bis(2,2,6,6-tetramethyl-4-piperidyl) sebacate (stabilizer), 1-ethyl-3-methylimidazolium bis(trifluoromethanesulfonyl)imide ([EMIM][NTf$_2$]/ionic liquid) and dichloromethane as solvent, prepared by mixing in an inert environment (glovebox). For this purpose, after the reactor had been purged with nitrogen, the catalyst solution was introduced into the reactor with a slightly positive pressure. After the solvent had been removed from the reactor by discharge and evaporation, the catalyst system heterogenized on the support was used for hydroformylation.

The feed mixture used was a hydrocarbon stream having the following composition:

|  | Amount (% by wt.) |
| --- | --- |
| 1-butene/isobutene | 19.14 |
| cis-2-butene | 19.10 |
| trans-2-butene | 28.40 |
| n-butane | 30.80 |
| isobutane | 0.02 |
| 2-methylbutane | 2.50 |

The feed mixture was guided into the reactor together with synthesis gas (molar synthesis gas:input mixture ratio=3.5:1) for hydroformylation at a gas volume flow rate of 390 ml/min. The hydroformylation was conducted at a temperature of 120° C. and a pressure of 10 bar. The total conversion of butenes (i.e. the conversion of all butenes present in the feed mixture) and the n/iso selectivity (ratio of linear to branched products) was ascertained by gas chromatography via the product composition.

After an experiment duration of 500 hours, total conversion of butenes was 27% and the n/iso selectivity 98%.

Experiment 2: Preparation and Analysis of a Catalyst System According to the Invention without Ionic Liquid The support used was a monolith of silicon carbide having a length of about 20 cm and a diameter of about 25 mm. The support was porous and was pretreated with a washcoat ($SiO_2$).

The support had 31 channels having a diameter of about 3 mm. The support was inserted into a reactor and contacted with a catalyst solution containing Rh(acac)(CO)$_2$, Biphephos (ligand), bis(2,2,6,6-tetramethyl-4-piperidyl) sebacate (stabilizer) and dichloromethane as solvent, prepared by mixing in an inert environment (glovebox). For this purpose, after the reactor had been purged with nitrogen, the catalyst solution was introduced into the reactor with a slightly positive pressure. After the solvent had been removed from the reactor by discharge and evaporation, the catalyst system heterogenized on the support was used for hydroformylation.

The feed mixture used was a hydrocarbon stream with virtually identical composition to that in Experiment 1. The feed mixture was guided into the reactor together with synthesis gas (molar synthesis gas:feed mixture ratio=3.5:1) for hydroformylation at a gas volume flow rate of 390 ml/min. The hydroformylation was conducted at a temperature of 120° C. and a pressure of 10 bar. The total conversion of butenes (i.e. the conversion of all butenes present in the feed mixture) and the n/iso selectivity (ratio of linear to branched products) was ascertained by gas chromatography via the product composition.

After an experiment duration of 500 hours, total conversion of butenes was 56% and the n/iso selectivity 97%.

Experiment 3: Preparation and Analysis of an SILP Catalyst System Not According to the Invention The catalyst system was prepared analogously to the preparation of the catalytically active composition Rh(II) in WO 2015/028284 A1.

The feed mixture used was a hydrocarbon stream having the following composition:

| | Amount (% by wt.) |
|---|---|
| 1-butene/isobutene | 27.40 |
| cis-2-butene | 15.00 |
| trans-2-butene | 25.00 |
| n-butane | 29.50 |
| isobutane | 0.02 |
| 2-methylbutane | 3.00 |

The feed mixture was guided into the reactor together with synthesis gas (molar synthesis gas:feed mixture ratio=3.5:1) for hydroformylation at a gas volume flow rate of 390 ml/min. The hydroformylation was conducted at a temperature of 120° C. and a pressure of 10 bar. The total conversion of butenes (i.e. the conversion of all butenes present in the feed mixture) and the n/iso selectivity (ratio of linear to branched products) was ascertained by gas chromatography via the product composition.

After an experiment duration of 500 hours, total conversion of butenes was 25% and the n/iso selectivity 92%.

It is thus apparent from the series of experiments that the heterogenized catalyst systems according to the invention without ionic liquid have the advantage over the known SILP systems or systems with ionic liquid that higher conversions and/or a higher linearity of the products (n/iso selectivity) can be achieved therewith.

The invention claimed is:

1. Process for hydroformylating C2 to C5 olefins, wherein the hydroformylation comprises one or more hydroformylation steps, wherein
in at least one hydroformylation step a feed mixture comprising the C2 to C5 olefins is subjected to a hydroformylation with synthesis gas in the presence of a catalyst system comprising a metal from group 8 or 9 of the Periodic Table of the Elements, at least one organic phosphorus-containing ligand and a stabilizer, in a reaction zone, wherein the feed mixture and the synthesis gas are passed over a support composed of a porous ceramic material on which the catalyst system is in heterogenized form,
the catalyst system does not comprise any ionic liquid; and
the support is a block of a ceramic material, to which a washcoat composed of the same or a different ceramic material with respect to the ceramic material of the support is applied.

2. The process according to claim 1, wherein a gaseous output comprising at least a portion of the product aldehydes formed and at least a portion of the unconverted olefins is withdrawn continuously from the reaction zone and the gaseous output is subjected to a physical separation step in which the gaseous output is separated into at least one phase rich in unconverted olefins and at least one phase rich in product aldehyde.

3. The process according to claim 1, wherein the organic phosphorus-containing ligand in the hydroformylation catalyst system has the general formula (VI)

R'-A-R''-A-R'''     (VI)

where R', R'' and R''' are each organic radicals, with the proviso that R' and R''' are not identical, and each A is a bridging —O—P(—O)2- group, where two of the three oxygen atoms —O— are respectively bonded to R' radical and R''' radical.

4. The process according to claim 1, wherein the stabilizer is an organic amine compound containing at least one 2,2,6,6-tetramethylpiperidine unit of formula (I):

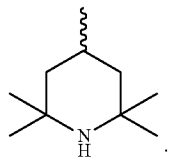

5. The process according to claim 1, wherein the porous ceramic material of which the support consists is selected from the group consisting of a silicate ceramic, an oxidic ceramic, a nitridic ceramic, a carbidic ceramic, a silicidic ceramic and mixtures thereof.

6. The process according to claim 5, wherein the silicate ceramic is selected from aluminosilicate, magnesium silicate, and mixtures thereof, the oxidic ceramic is selected from γ-alumina, α-alumina, titanium dioxide, beryllium oxide, zirconium oxide, aluminium titanate, barium titanate, zinc oxide, iron oxides (ferrites) and mixtures thereof; the nitridic ceramic is selected from silicon nitride, boron nitride, aluminium nitride and mixtures thereof; the carbidic ceramic is selected from silicon carbide, boron carbide, tungsten carbide or mixtures thereof; and the silicidic ceramic is molybdenum silicide.

7. The process according to claim 5, wherein the porous ceramic material of which the support consists is a carbidic ceramic.

8. The process according to claim 6, wherein the carbidic ceramic is selected from silicon carbide, boron carbide, tungsten carbide or mixtures thereof.

9. The process according to claim 1, wherein the amount of the washcoat on the support is ≤20% by weight, based on the total amount of the support.

10. The process according to claim 1, wherein the support composed of the ceramic material has one or more channels in main through-flow direction.

11. The process according to claim 1, wherein the hydroformylation step is conducted at a temperature in the range from 65 to 200° C.

12. The process according to claim 1, wherein the pressure in the hydroformylation step is not greater than 35 bar.

13. The process according to claim 2, wherein the organic phosphorus-containing ligand in the hydroformylation catalyst system has the general formula (VI)

R'-A-R''-A-R'''     (VI)

where R', R'' and R''' are each organic radicals, with the proviso that R' and R''' are not identical, and each A is a bridging —O—P(—O)2- group, where two of the three oxygen atoms —O— are respectively bonded to R' radical and R''' radical.

14. The process according to claim 2, wherein the stabilizer is an organic amine compound containing at least one 2,2,6,6-tetramethylpiperidine unit of formula (I):

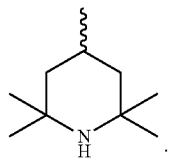

15. The process according to claim 2, wherein the porous ceramic material of which the support consists is selected from the group consisting of a silicate ceramic, an oxidic ceramic, a nitridic ceramic, a carbidic ceramic, a silicidic ceramic and mixtures thereof.

16. The process according to claim 15, wherein the silicate ceramic is selected from aluminosilicate, magnesium silicate, and mixtures thereof, the oxidic ceramic is selected from γ-alumina, α-alumina, titanium dioxide, beryllium oxide, zirconium oxide, aluminium titanate, barium titanate, zinc oxide, iron oxides (ferrites) and mixtures thereof; the nitridic ceramic is selected from silicon nitride, boron nitride, aluminium nitride and mixtures thereof; the carbidic ceramic is selected from silicon carbide, boron carbide, tungsten carbide or mixtures thereof; and the silicidic ceramic is molybdenum silicide.

17. The process according to claim 15, wherein the porous ceramic material of which the support consists is a carbidic ceramic.

18. The process according to claim 16, wherein the carbidic ceramic is selected from silicon carbide, boron carbide, tungsten carbide or mixtures thereof.

19. The process according to claim 2, wherein the amount of the washcoat on the support is ≤20% by weight, based on the total amount of the support.

20. The process according to claim 2, wherein the support composed of the ceramic material has one or more channels in main through-flow direction.

* * * * *